United States Patent [19]

Hayano et al.

[11] Patent Number: 4,966,457
[45] Date of Patent: Oct. 30, 1990

[54] INSPECTING APPARATUS FOR DETERMINING PRESENCE AND LOCATION OF FOREIGN PARTICLES ON RETICLES OR PELLICLES

[75] Inventors: Fuminori Hayano, Kamakura; Kazunori Imamura, Tokyo; Sunao Murata, Kawasaki, all of Japan

[73] Assignee: Nikon Corporation, Tokyo, Japan

[21] Appl. No.: 298,920

[22] Filed: Jan. 19, 1989

[30] Foreign Application Priority Data

Jan. 21, 1988 [JP] Japan ................... 63-11725

[51] Int. Cl.⁵ .............................. G01N 21/88
[52] U.S. Cl. .................... 356/237; 356/239; 356/338; 250/572
[58] Field of Search ............. 356/237, 239, 73, 338, 356/432, 445, 448; 250/562, 563, 572

[56] References Cited

U.S. PATENT DOCUMENTS

| | | | |
|---|---|---|---|
| 4,265,545 | 5/1981 | Slaker | 250/572 |
| 4,468,120 | 8/1984 | Tanimoto et al. | 356/237 |
| 4,610,541 | 9/1986 | Tanimoto et al. | 356/237 |
| 4,669,875 | 6/1987 | Shiba et al. | 356/237 |

*Primary Examiner*—Vincent P. McGraw
*Assistant Examiner*—S. A. Tuanga
*Attorney, Agent, or Firm*—Shapiro and Shapiro

[57] ABSTRACT

A defect inspecting apparatus for determining the presence of a defect element adhering to either of the front and back surfaces of a thin film-like object to be inspected (the object having a light-transmitting property) applies two light beams of different wavelengths to a surface of the object and varies the incident angle of the light beams. A first photoelectric detector receives light of the two light beams reflected by or transmitted by the object, and a second photoelectric detector receives light of the two light beams scattered by the defect element. A discriminator determines the surface of the object to which the defect element adheres based on detection outputs of the photoelectric detectors.

13 Claims, 7 Drawing Sheets

INSPECTING APPARATUS FOR DETERMINING PRESENCE AND LOCATION OF FOREIGN PARTICLES ON RETICLES OR PELLICLES

BACKGROUND OF THE INVENTION

1. Field of the Invention

This invention relates to an apparatus inspection apparatus for determining the presence and location of a tiny foreign particle such as dust, and in particular to an inspecting apparatus for determining the presence and location of a defect such as a tiny foreign particle adhering to the surface of a photomask, a reticle or a semiconductive wafer used in the manufacturing process of integrated circuits or of a pellicle or the like for protecting the photomask or the reticle from dust or the like.

2. Related Background Art

In the photolithography process which is one of the manufacturing processes of integrated circuits, transfer of a circuit pattern to a semiconductive wafer is effected by the use of a reticle or a photomask (hereinafter simply referred to as the reticle).

In this case, if a foreign particle such as dust adheres to the reticle, it presents itself as a defect of the circuit pattern when the transfer thereof to the semiconductive wafer is effected, and this causes a reduction or the like in yield.

A foreign particle inspecting apparatus for determining whether a tiny foreign particle adheres to the surface of a reticle or the like is known from U S Patents Nos. 4,468,120 and 4,610,541. This foreign particle inspecting apparatus is designed such that light is applied to an object to be inspected and scattered light from a foreign particle is detected by the use of photoelectric detector means, whereby the information regarding the position and size of the foreign particle on the surface of the reticle or the like is obtained, and such apparatus is useful to prevent an inconvenience such as the above-mentioned reduction in yield.

Also, recently, as a method of preventing a tiny foreign particle from adhering to the surface of a substrate such as a reticle, it has been the practice to mount a transparent thin film called a pellicle (a foreign particle adherance preventing film) on the surface of the reticle or the like. That is, the pellicle is mounted on that reticle or the like through a support frame to cover the surface of the reticle or the like with the pellicle, thereby preventing a foreign particle from directly adhering to the reticle or the like. Where projection exposure is effected by an exposure apparatus by the use of the reticle or the like covered with the pellicle, even if a foreign particle adheres to the surface of the pellicle, the image of the foreign particle is not focused and formed on the surface of an object to be projected, i.e., a semiconductive wafer, and thus, such image of the foreign particle is not transferred.

However, where the foreign particle adhering to the surface of the pellicle is relatively large, exposure irregularity may occur at a position on the surface of the semiconductive wafer which corresponds to the foreign particle. Also, a foreign particle adhering to the lower surface of the pellicle, i.e., that surface of the pellicle which is adjacent to the reticle, even if not so large as to cause exposure irregularity, may leave the surface of the pellicle and adhere to the surface of the reticle or the like, and if such foreign particle adheres to the surface of the reticle, the image of the foreign particle will be transferred to the semiconductive wafer.

Accordingly, even where a pellicle is used, it is necessary to determine the position and size of a foreign particle adhering to the pellicle and further, it is also necessary to discriminate whether the foreign particle adheres to the upper surface of the pellicle (the surface opposite to the reticle) or the lower surface of the pellicle (the surface which is adjacent to the reticle).

Where as described above, a pellicle is used to cover the reticle or the like, it is necessary to determine not only the position and size of a foreign particle adhering to the pellicle, but also to which of the upper surface or the lower surface (i.e., the outer surface or the inner surface) of the pellicle the foreign particle adheres, before as well as after the pellicle is mounted on the reticle or the like. However, the foreign particle inspecting apparatus according to the prior art has suffered from the problem that although it can know the position and size of the foreign particle on the surface of the pellicle, It cannot discriminate to which of the upper surface of the pellicle (the surface opposite to the reticle or the like or the lower surface of the pellicle (the surface which is adjacent to the reticle) the foreign particle adheres, because the pellicle is very thin.

SUMMARY OF THE INVENTION

Accordingly, it is an object of the present invention to solve the above-noted problem peculiar to the prior-art apparatus and to provide a defect inspecting apparatus which can discriminate not only the position and size of foreign particle adhering to the surface of a thin film-like object to be inspected such as a pellicle, bu& also to which of the upper surface or the lower surface of the object to be inspected the foreign particle adheres.

To achieve the above object, the defect inspecting apparatus of the present invention is characterized by the provision of applying means for applying two light beams of different wavelengths to one of the upper and lower surfaces of a thin filmlike object to be inspected, incident angle varying means capable of varying the incident angle of said two light beams, first photoelectric detector means for receiving light of said two light beams reflected by or transmitted by the object to be inspected, second photoelectric detector means for receiving light of said two light beams scattered by a foreign particle, and discriminating means for discriminating the surface of the object to be inspected to which the foreign particle adheres on the basis of the detection signal of said first photoelectric detector means and the detection signal of said second photoelectric detector means.

Also, with the incident angle of the two beams remaining fixed, the angle formed between the detection center axis (the optic axis) of said second photoelectric detector means and the object to be inspected may be varied and said second photoelectric detector means may be endowed with the function of said first photoelectric detector means.

According to the present invention constructed as described above, not only the presence of a foreign particle adhering to the object to be inspected but also to which of the upper surface or the lower surface of said object the foreign particle adheres can be discriminated accurately and easily.

Other objects, features and effects of the present invention will become fully apparent from the following detailed description taken in conjunction with the accompanying drawings.

DESCRIPTION OF THE PREFERRED EMBODIMENTS

Generally, a pellicle has its film thickness set so that the transmittance thereof is greatest for the exposure wavelength of an exposure apparatus for transferring a circuit pattern to a semiconductive wafer in the case of perpendicular incidence. It has also been confirmed by the inventors that if the wavelength or the incident angle of the incident light differs due to the interference of light by a thin film, the transmittance of the light through the pellicle also varies.

Figure 1:
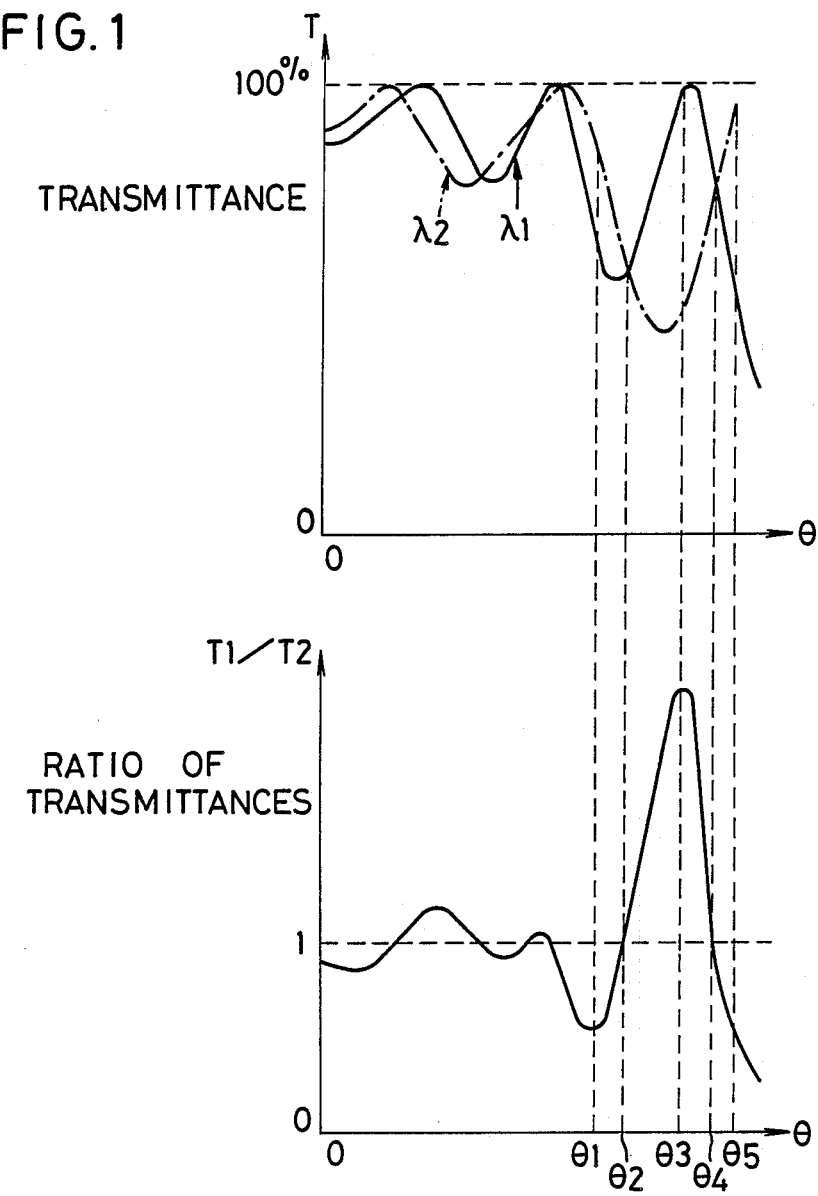
FIG. 1 is a graph showing the dependency, on the incident angle, of the transmittance of a pellicle which is an object to be inspected by an apparatus according to an embodiment of the present invention.

The manner of variation in the transmittance will now be described with reference to FIG. 1. FIG. 1 shows the dependency, on the incident angle $\theta$ (the horizontal axis), of the transmittance T (the vertical axis) of light through the pellicle when light of two different wavelengths $\lambda_1$ and $\lambda_2$ is incident on the same pellicle, and the dependency, on the incident angle $\theta$, of the ratio $T_1/T_2$ (the vertical axis) of the transmittance $T_1$ of the pellicle for the light of wavelength $\lambda_1$ and the transmittance $T_2$ of the pellicle for the light of wavelength $\lambda_2$. In FIG. 1, the solid line indicates the transmittance for the light of wavelength $\lambda_1$ and the dot-and-dash line indicates the transmittance for the light of wavelength $\lambda_2$. When the incident angle is $\theta_2$ and $\theta_4$, the transmittance $T_1$ of the pellicle for the light of wavelength $\lambda_1$ is equal to the transmittance $T_2$ of the pellicle for the light of wavelength $\lambda_2$, that is, $T_1 = T_2$, and further, when the incident angle is $\theta_1$ and $\theta_5$, the relation between the two transmittances $T_1$ and $T_2$ is $T_1 < T_2$, and when the incident angle is $\theta_3$, the relation between the two transmittances $T_1$ and $T_2$ is $T_1 > T_2$.

Now, if the pellicle which is the object to be inspected has the transmittance characteristic as shown in FIG. 1 for the light of two wavelengths $\lambda_1$ and $\lambda_2$, where the light of two wavelengths $\lambda_1$ and $\lambda_2$ is applied from above to one of the front and back surfaces of the pellicle, when the incident angle $\theta$ of the light is $\theta = \theta_2$ or $\theta = \theta_4$, the absolute quantity of the light is sometimes reduced on the pellicle surface to which the light is applied (hereinafter referred to as the "upper surface") and the pellicle surface opposite thereto (hereinafter referred to as the "lower surface"), but the ratio of quantity of light between the light of wavelengths $\lambda_1$ and $\lambda_2$ never changes between the upper surface and the lower surface of the pellicle. In contrast, if the light of wavelengths $\lambda_1$ and $\lambda_2$ is applied at the incident angle of $\theta = \theta_1$ or $\theta = \theta_5$, the light of wavelength $\theta_2$ is more transmitted in the lower surface of the pellicle than the light of wavelength $\theta_1$, and if the light is applied at the incident angle of $\theta = \theta_3$, this relation is reversed, that is, the light of wavelength $\theta_1$ is more transmitted than the light of wavelength $\lambda_2$.

Assuming that when the light of two wavelengths $\lambda_1$ and $\lambda_2$ are applied to the pellicle at the incident angle of $\theta = \theta_3$, the quantity of scattered light from a foreign particle adhering to the pellicle which corresponds to the wavelength $\theta_1$ is $I_l$ and the quantity of scattered light from said foreign particle which corresponds to the wavelength $\lambda_2$ is $I_2$, where that foreign particle adheres to the upper surface of the pellicle, the quantities of said scattered light become substantially equal ($I_l \approx I_2$) if the quantities of incident light of these two wavelengths $\lambda_1$ and $\lambda_2$ are the same. However, where the foreign particle adheres to the lower surface of the pellicle, the light of wavelength $\lambda_1$ is more transmitted through the pellicle because the light of wavelength $\lambda_1$ is higher in transmittance than the light of wavelength $\lambda_2$, and the light of wavelength $\lambda_1$ irradiates the foreign particle. Therefore, the quantity of scattered light $I_l$ from the foreign particle by the light of wavelength $\lambda_1$ becomes greater than the quantity of scattered light $I_2$ by the light of wavelength $\lambda_2$. Accordingly, depending on whether the ratio $I_1/I_2$ between the quantities of scattered light from the foreign particle by the two wavelengths $\lambda_1$ and $\lambda_2$ is 1, it becomes possible to discriminate to which of the upper surface and the lower surface of the pellicle the foreign particle adheres.

Besides the above-described method of discrimination, the light of two wavelengths $\lambda_1$ and $\lambda_2$ may be caused to be incident at two different incident angles. That is, as seen from the ratio of transmittances of FIG. 1, when the light of two wavelengths $\lambda_1$ and $\lambda_2$ are applied, for example, at a combination of incident angles $\theta_1$ and $\theta_3$ or a combination of incident angles $\theta_5$ and $\theta_3$ with respect to those two incident angles and the ratio $I_1/I_2$ of the quantities of scattered light from the foreign particle adhering to the pellicle is compared, the ratio $I_1/I_2$ of the quantities of scattered light is $I_1/I_2 < 1$ at the incident angle of $\theta = \theta_1$ for a foreign particle adhering to the lower surface of the pellicle, and the ratio $I_1/I_2$ is reversed to $I_1/I_2 > 1$ at the incident& angle of $\theta = \theta_3$. In contrast, for a foreign particle adhering to the upper surface of the pellicle, the ratio $I_1/I_2$ of the quantities of scattered light is always substantially 1 even if the incident angle $\theta_1$ is $\theta_1$ or $\theta_3$. The same thing also occurs a& other combinations of incident angles (e.g., $\theta = \theta_5$ and $\theta = \theta_3$). Thus, it becomes possible to discriminate the surface of the pellicle to which the foreign particle adheres.

As described above, the transmittance of the pellicle differs depending on the wavelength of the applied light and the incident angle of the light, and for a given wavelength, at a certain incident angle, the quantity of light transmitted through the upper surface of the pellicle to the back surface thereof becomes small. Accordingly, when light of two different wavelengths is applied to the pellicle surface at the same incident angle, the ratio of the quantities of scattered light from the foreign particle on the pellicle differs between a foreign particle adhering to the upper surface of the pellicle and a foreign particle adhering to the lower surface of the pellicle. Thus, it becomes possible to discriminate the surface of the pellicle to which a foreign particle adheres.

Further, as a method discrete from the abovedescribed two methods, laser beams of wavelengths $\lambda_1$ and $\lambda_2$ may be applied to a foreign particle on the pellicle at a predetermined incident angle and scattered light obtained from that foreign particle may be received with the light receiving angle (the vertical angle relative to the pellicle) changed, to thereby obtain a similar effect. That is, where scattered light is received on the same side as the application of the laser beams (the upper surface side of the pellicle), the scattered light from a foreign particle adhering to the lower surface of the pellicle is transmitted through the pellicle and thereafter received and therefore, if the light receiving angle is changed, there appears a variation in the quantity of scattered light correspondingly to the dependency of the transmittance of the pellicle on the incident angle. For example, when the light receiving angle is $\theta_3$ (at this time, the transmittance of the pellicle for the light of wavelength $\lambda_1$ is greater than the transmittance of the pellicle for the light of wavelength $\lambda_2$), the quantities of received light when the laser beams of wavelengths $\lambda_1$ and $\lambda_2$ are applied are the same for a foreign particle adhering to the upper surface of the pellicle, but for a foreign particle adhering to the lower. surface of the pellicle, the scattered light when the laser beam of wavelength $\lambda_1$ is greater in quantity of received light than the scattered light when the laser beam of wavelength $\lambda_2$ is applied. By the magnitude of this quantity of received light, it becomes possible to discriminate to which surface of the pellicle a foreign particle adheres. Of course, it is also possible to bring about an optimum condition by changing each of the incident angle and the light receiving angle.

Figure 2:
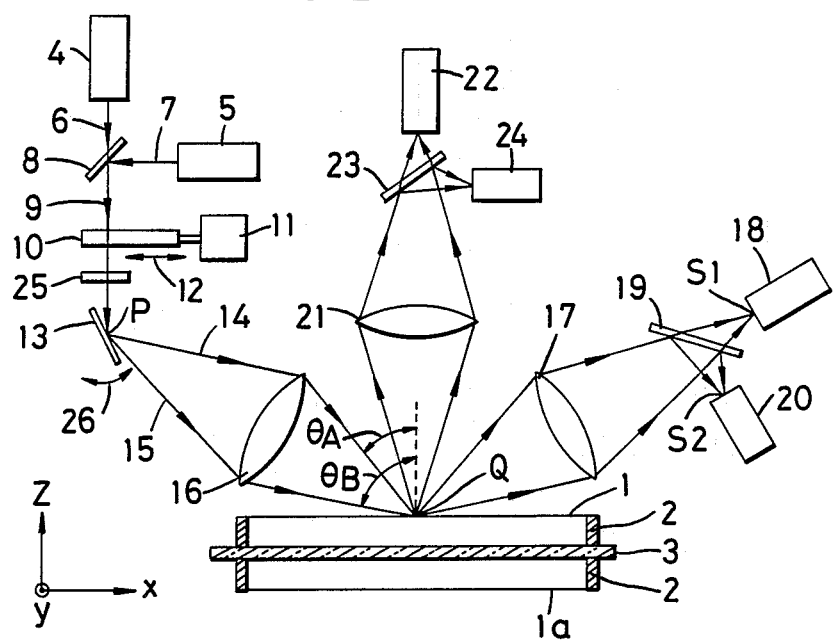
FIG. 2 schematically shows the construction of a defect inspecting apparatus according to a first embodiment of the present invention.

Referring to FIG. 2 which schematically shows the construction of a first embodiment, a pellicle 1 is mounted on a reticle or a photomask (hereinafter represented as the "reticle") 3 through a support frame 2. The reticle 3 is placed on a stage, not shown, which is movable in x direction and y direction perpendicular to the plane of the drawing sheet. Accordingly, by this stage being moved in x direction and y direction, foreign particle inspection at any position of the pellicle 1 becomes possible.

A laser source 4 outputting a light beam of wavelength $\lambda_1$ and a laser source 5 outputting a light beam of wavelength $\lambda_2$ are disposed at the upper surface side of the pellicle 1. The quantity of light of the light beam of wavelength $\lambda_1$ and the quantity of light of the light beam of wavelength $\lambda_2$ are set so as to be substantially equal to each other. Laser beams 6 and 7 output from the two laser sources 4 and 5 respectively, are made into a laser beam 9 on the same axis by a dichroic mirror 8. This dichroic mirror 8 has the wavelength selecting property of not reflecting but transmitting the light of wavelength $\lambda_1$ and not transmitting but reflecting the light of wavelength $\lambda_2$, and the laser beam 9 including the two wavelengths $\lambda_1$ and $\lambda_2$ passed therethrough further passes through a variable density filter (variable D filter) 10 disposed in the optical path. The variable ND filter 10 differs in transmittance depending on the position through which the light passes, and the variable ND filter 10 is moved in the direction of arrow 12 by a driver 11, whereby the quantities of light of the laser beams of two wavelengths $\lambda_1$ and $\lambda_2$ on the optical path can be changed at the same time and always at the same light decreasing rate.

It is for the following reason that by the driver 11 and the variable ND filter 10, the quantities of light of the applied laser beam 9 are adjusted at the same rate irrespective of the difference in wavelength. Firstly, as already described, where light is applied to a foreign particle lying on the lower surface of the pellicle 1, the incident angle $\theta$ of the light beam is changed to reliably accomplish the discrimination of the surface to which the foreign particle adheres, but at this time, the transmittance of the pellicle 1 is low depending on the incident angle and particularly, a sufficient quantity of scattered light is not obtained from a tiny foreign particle adhering to the lower surface of the pellicle 1, and this may lead to a case where the surface to which the foreign particle adheres is discriminated wrongly due to a reduction in the S/N ratio of the detection signal. Conversely, in the case of a large foreign particle, the quantity of scattered light is too strong and it is necessary to prevent the detection signal from being saturated. That is, the purpose is to obtain an appropriate quantity of scattered light in any case. A second reason is attributable to the fact that although in the present invention, light of two different wavelengths is applied to a foreign particle, the surface to which the foreign particle adheres may be discriminated wrongly unless at this time, the ratio of the quantities of light of two wavelengths is always the same. This is because, to effect said adjustment of the quantity of light discretely by lights of two wavelengths, adjustment of the quantity of light is effected discretely in the optical path of the laser beam 6 and the optical path of the laser beam 7, for example, in FIG. 2, and it is more difficult in control to make the ratio of the two quantities of light always constant than to adjust the quantity of light of the laser beam 9 including both of the two wavelengths $\lambda_1$ and $\lambda_2$ on the same optical path.

The laser beam 9 transmitted through the variable ND filter 10 is polarized by a polarizing plate 25 so as to obliqueLy enter the pellicle 1 by S-polarization (polarization perpendicular to the plane of the drawing sheet), whereafter it is deflected within the range of the optical path 14 and the optical path 15 by a variable angle mirror 13 being rotated in the direction of arrow 26, and then is refracted by a lens 16 and is incident on a point Q on the pellicle 1 In this case, the center of rotation P of the variable angle mirror 13 is in optically conjugate relationship with the point Q on the pellicle 1. Accordingly, by changing the angle of the variable angle mirror 13, it becomes possible to continuously change the incident angle of the laser beam 9 onto the pellicle 1 within the range from the incident angle $\theta_A$ to $\theta_B$ and always irradiate the point Q on the pellicle 1. The incident angle of the laser beam 9 may preferably be in the range of 10°-90°.

A lens 17 and a photoelectric detector 18 for receiving the regularly reflected light of the laser beam 9 reflected by the pellicle 1 are disposed on the upper surface side of the pellicle 1. The photoelectric detector 18 is placed at a point $S_1$ optically conjugate with the irradiated position Q on the pellicle 1. Therefore, it can always receive the regularly reflected light even if the incident angle of the laser beam 9 is changed. A dichroic mirror 19 is placed in the optical path between the lens 17 and the photoelectric detector 18, and the reqularly reflected light having branched off by the dichroic mirror 19 is received by a photoelectric detector 20 placed at a point $S_2$ also optically conjugate with the irradiated position Q on the pellicle 1. Accordingly, the photoelectric detector 20 can also always receive the regularly reflected light even if the incident angle of the laser beam 9 is changed. The dichroic mirror 19 has the wavelength selecting property of not reflecting but transmitting the light of wavelength $\lambda_1$ and not transmitting but reflecting the light of wavelength $\lambda_2$. Accordingly, the photoelectric detector 18 receives only the regularly reflected light of wavelength $\lambda_1$, and the photoelectric detector 20 receives only the regularly reflected light of wavelength $\lambda_2$, and these detectors output photoelectric signals proportional to the quantities of light received thereby.

Figure 3:
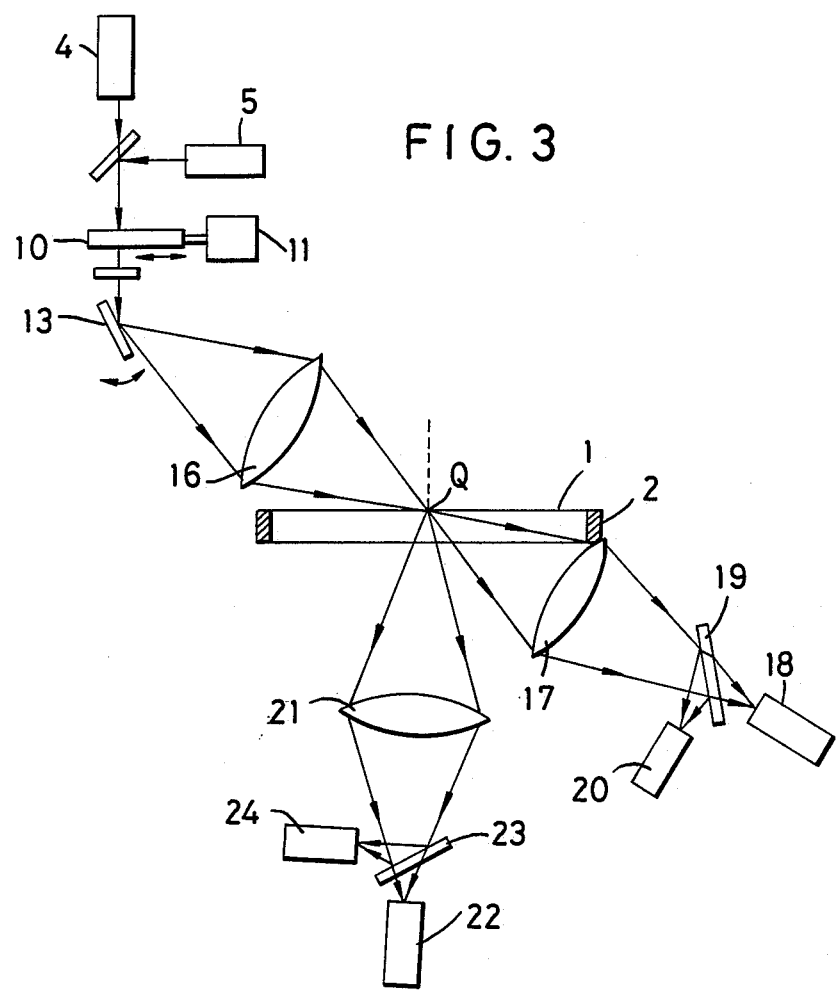
FIG. 3 schematically shows the construction of a defect inspecting apparatus according to a second embodiment of the present invention.

The reason why as described above, the detecting optical system comprising the lens 17, the two photoelectric detectors 13, 20 and the dichroic mirror 19 for receiving the regularly reflected light of the laser beam 9 by the pellicle 1 is disposed at the position for receiving the regularly reflected light by the pellicle 1 is that in a state in which the pellicle 1 is mounted on the reticle 3 through the support frame 2, it is difficult to receive the light transmitted through the pellicle 1 and accurately measure the transmittance directly from the transmitted light. That is, measurement of the transmittance of the pellicle 1 on the upper side which is the surface to be inspected becomes quite difficult under the influence of not only the transmittance of the pellicle 1 but also the transmittance of the reticle 3 and further, in a case where as shown in FIG. 2, pellicles are mounted on both of the upper and lower surfaces of the reticle 3 the transmittance not only of the pellicle 1 on that surface side (the upper side) to which the laser beam is applied, but also of the pellicle 1a attached to the opposite side (the lower side). Accordingly, in the inspection of the foreign particle on the pellicle 1 in the state in which as shown in FIG. 2, the pellicle 1 has already been mounted on the reticle 3, the regularly reflected light from the pellicle 1 is detected with respect to the two wavelengths $\lambda_1$ and $\lambda_2$ without the transmittance of the pellicle 1 which is the surface to be inspected being directly measured, and when there is no absorption in the pellicle 1 for these two wavelengths $\lambda_1$ and $\lambda_2$, the transmittance of the pellicle 1 is surmised from the relation that the sum of the transmittance and the reflectance is 1. Of course, where the pellicle is not mounted on the reticle, but as shown in FIG. 3, the pellicle 1 is a single piece, the detecting optical system may be disposed on the opposite side (the lower surface side) to the side (the upper surface side) to which the light is applied, with respect to the pellicle 1, and the transmittance of the pellicle 1 may be directly measured.

In FIG. 2, a light receiving lens 21 and photoelectric detectors 22 and 24 for detecting the scattered light from a foreign particle on the pellicle 1 are disposed on the upper surface of the pellicle 1. A dichroic mirror 23 is disposed in the optical path between the light receiving lens 21 and the photoelectric detector 22, and is designed to transmit only the light of wavelength $\lambda_1$ and direct it to the photoelectric detector 22 and reflect only the light of wavelength $\lambda_2$ and direct it to the photoelectric detector 24. The scatterad light detecting optical system, i.e., the light receiving lens 21, the dichroic mirror 23 and the photoelectric detectors 22, 24 may be disposed anywhere on that surface side (the upper side) to which the Light outside the optical path of the regularly reflected light of the laser beam 9 is applied and on the path of the scattered light. Of course, if the angle at which the light should be decreased when the scattered light from a foreign particle on the lower surface is transmitted through the pellicle is determined, there will be provided a greater effect. Further, where the pellicle 1 is not mounted on the reticle 3 and foreign particle inspection is effected for the pellicle 1 as a single piece, the scattered light detecting optical system 21-24 may be disposed on the opposite surface side (the lower side) to the surface side to which the light is applied, as shown in FIG. 3, to receive the scattered light. Also, the defect detecting apparatus of the first embodiment shown in FIG. 2 may incorporate therein a microscope with a stage finely movable in X and Y directions. In such case, there is the advantage that visual inspection of a foreign particle can be done at the same time.

Figure 4:
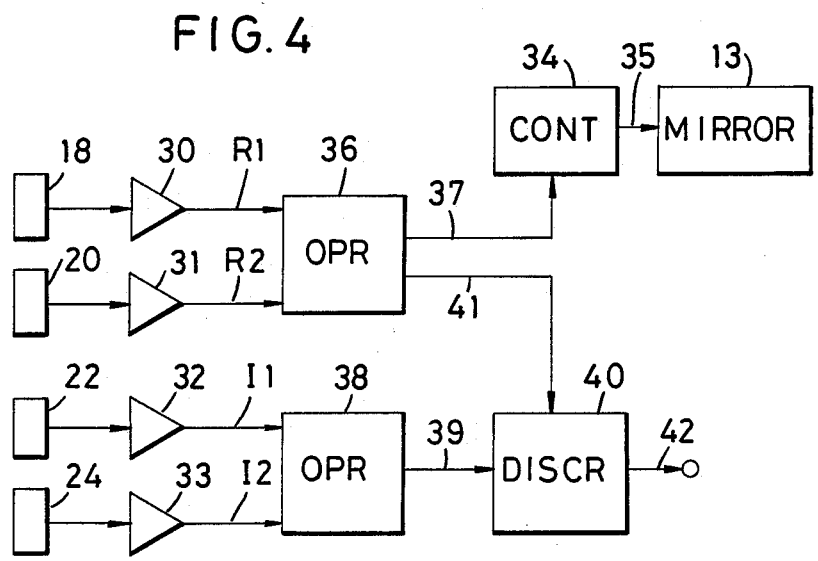
FIG. 4 is a circuit block diagram showing the construction of a signal processing circuit applied to the apparatuses of the embodiments of FIGS. 2 and 3.

A processing device for the photoelectric signals output from the photoelectric detectors 18, 20, 22 and 24 will now b<described with reference to FIG. 4.

The photoelectric outputs of the photoelectric detectors 18, 20, 22 and 24 are amplified by amplifiers 30, 31, 32 and 33, respectively, whereby electrical signals $R_1$, $R_2$, $I_1$ and $I_2$ proportional to the quantities of received light are obtained. That is, the photoelectric signal $R_1$ is obtained for the light of wavelength $\lambda_1$ of the regularly reflected light by the pellicle 1, the photoelectric signal $R_2$ is obtained for the light of wavelength $\lambda_2$, the photoelectric signal $I_f$ is obtained for the light of wavelength $\lambda_1$ of the scattered light from a foreign particle adhering to the pellicle 1, and the photoelectric signal $I_2$ is obtained for the light of wavelength $\lambda_2$.

An angle is designated by an output signal 35 from a control unit 34 and the variable angle mirror 13 is driven to vary the incident angle of the laser beam 9. At this time, the photoelectric signals $R_1$ and $R_2$ are first converted into reflectances $R_1(\theta)$ and $R_2(\theta)$, respectively, as functions of the incident angle $\theta$, in an operation unit 36. Further, in the operation unit 36, the ratio of the reflectances $R_1(\theta)$ and $R_2(\theta)$ of the pellicle 1 for the light of wavelengths $\lambda_1$ and $\lambda_2$ is obtained, and the angle $\theta_0$ for which the ratio of the reflectances $R_1(\theta)$ and $R_2(\theta)$ becomes greatest is found, and a signal 37 is output to the control unit 34 to drive the variable angle mirror 13 so that the laser beam 9 may enter the pellicle 1 at this incident angle $\theta_0$.

After the variable angle mirror 13 is driven and the reflectances $R_1(\theta)$ and $R_2(\theta)$ of the pellicle 1 for the wavelengths $\lambda_1$ and $\lambda_2$ are found, the foreign particle to be inspected is moved to the irradiated position Q on the pellicle 1 by an x-y driving device, not shown. At this time, the photoelectric electrical signals $I_1$ and $I_2$ of the scattered light from said foreign particle for the applied light of wavelengths $\lambda_1$ and $\lambda_2$ are obtained as $I_1(\theta)$ and $I_2(\theta)$ at an angle fixed to the incident angle $\theta_0$ previously found by the operation unit 36 with the variable angle mirror 13 driven by the control unit 34. In an operation unit 38, the ratio of the photoelectric signals $I_1(\theta_0)$ and $I_2(\theta_0)$ to the wavelengths $\lambda_1$ and $\theta_2$ is found, and the output signal 39 thereof is input to a discrimination unit 40. In the discrimination unit 40, to which of the irradiated surface side (the upper surface) of the pellicle 1 or the opposite surface side (the lower surface) to the irradiated surface said foreign particle adheres is disciminated from the ratio of $I_1(\theta_0)$ and $I_2(\theta_0)$. The discrimination is accomplished from the magnitude relation between a certain threshold value e and the ratio of $I_1(\theta)$ and $I_2(\theta)$, and the then threshold value $\alpha$ is found from the previously found reflectances $R_1(\theta)$ and $R_2(\theta)$ in the operation unit 36, and the threshold value signal 41 thereof is input to the discrimination unit 40, whereby the surface to which said foreign particle adheres is discriminated, and the result of this discrimination, for example, a binarized digital signal 42 corresponding to the state in which said foreign particle adheres to the upper surface or the lower surface, is output.

A first method of discriminating the surface to which the foreign particle adheres will now be described with reference to the flow chart of FIG. 5.

Light of wavelengths $\lambda_1$ and $\lambda_2$ is first applied to the surface of the pellicle (step 50), and the variable angle mirror 13 is driven by the control unit 34 to change the incident angle $\theta$ of the laser beam 9 onto the pellicle 1 within a predetermined range from $\theta_A$ to $\theta_B$. The incident angle $\theta$ may be continuously changed or may be separately changed every several degrees. Where, for example, a galvano scanner is used as the variable angle mirror 13, the incident angle $\theta$ can be known from an angle detection signal output from the galvano scanner. At the same time, the regularly reflected light from the pellicle 1 for the lights of wavelengths $\lambda_1$ and $\lambda_2$ are received by the photoelectric detectors 18 and 20, respectively, and the reflectances $R_1(\theta)$ and $R_2(\theta)$ for the light of respective wavelengths are detected as functions of the incident angle $\theta$ (step 51).

Next, in order to find the incident angle $\theta_0$ for which the ratio of the transmittances of the pellicle 1 for the lights of wavelengths $\lambda_1$ and $\lambda_2$, i.e., the ratio of $1 - R_1(\theta)$ and $1 - R_2(\theta)$, is greatest within the range of $\theta_A$ to $\theta_B$, the incident angle $\theta_0$ for which the absolute value of $\log[(1 - R_1(\theta))/(1 - R_2(\theta))]$ becomes greatest is determined in the operation unit 36 (step 52). Subsequently, the variable angle mirror 13 is driven to set the incident angle of the laser beam 9 to $\theta_0$ (step 53).

Since at the incident angle $\theta_0$, the ratio of the transmittances of the pellicle 1 for the light of wavelengths $\lambda_1$ and $\lambda_2$ is greatest, discrimination of the surface to which the foreign particle adheres becomes easier than when the light of two wavelengths is applied at the other [incident angles. To discriminate the surface to which the foreign particle adheres from the ratio of the quantities of scattered light $I_1(\theta_0)$ and $I_2(\theta_0)$ from the foreign particle to the light of wavelengths $\lambda_1$ and $\lambda_2$ at the incident angle $\theta_0$, the magnitude relation between the ratio of the photoelectric signals $I_1(\theta_0)$ and $I_2(\theta_0)$ of the quantities of scattered light and a certain threshold value $\alpha$ may be examined, and that threshold value $\alpha$ is determined by the reflectances $R_1(\theta_0)$ and $R_2(\theta_0)$ of the pellicle 1 for the light of wavelengths $\lambda_1$ and $\lambda_2$ at the incident angle $\theta_0$. For example, where for the light of wavelength $\lambda_1$, $R_1(\theta_0) = 0\%$, that is, the transmittance is 100%, and for the light of wavelength $\lambda_2$, $R_2(\theta_0) = 50\%$, that is, the transmittance is 50%, the threshold value $\alpha$ is set to $\alpha = |\log[(1 - R_1(\theta_0) + 1 - R_2(\theta_0))/2]|$ every time depending on the respective transmittances at the incident angle $\theta_0$ in such a manner that the threshold value $\alpha$ is set to a value corresponding to the mean value of the transmittances, i.e., 75%, for example, $\alpha = |\log 0.75|$ (step 54).

Subsequently, the foreign particle to be inspected is moved to the irradiated position Q of the laser beam 9 (step 55). Where the first embodiment shown in FIG. 2 is incorporated, for example, into a microscope having a stage movable in X and Y directions, if the irradiated position Q is set on the optic axis of an objective lens, the work of moving the foreign particle to be inspected to the center of the field of view while visually observing the foreign particle can be accomplished easily. Further, if an image pick-up element such as an ITV is connected, observation of the foreign particle by the ITV and measurement of the quantity of scattered light can be accomplished at a time.

Subsequently, the scattered light from said foreign particle for the wavelengths $\lambda_1$ and $\lambda_2$ at the incident angle $\theta_0$ is received by the photoelectric detectors 22 and 24 to obtain quantity-of-light signals $I_1(\theta_0)$ and $I_2(\theta_0)$ (step 56). On the basis of these measured values $I_1(\theta_0)$ and $I_2(\theta_0)$, the absolute value of the ratio of $I_1(\theta_0)$ and $I_2(\theta_0)$, i.e., $\log[I_1(\theta_0)/I_2(\theta_0)]$, is found in the operation unit 38 of FIG. 4, and then the surface to which the foreign particle adheres is discriminated in the discrimination unit 40 by the magnitude relation between said absolute value and the threshold value previously determined at step 54 (step 57).

As already described, the quantity of light of wavelength $\lambda_1$ and the light of wavelength $\lambda_2$ applied to the pellicle 1 are substantially equal. Accordingly, if the foreign particle adheres to the upper surface (the irradiated surface side) of the pellicle 1, the photoelectric signal $I_1(\theta_0)$ of the quantity of scattered light from the foreign particle for the light of wavelength $\lambda_1$ and the photoelectric signal $I_2(\theta_0)$ of the quantity of scattered light from the foreign particle for the light of wavelength $\lambda_2$ are substantially equal, and the absolute value of $\log[I_1(\theta_0)/I_2(\theta_0)]$ becomes substantially zero. In contrast, if the foreign particle adheres to the lower surface (the surface side opposite to the irradiated surface) of the pellicle 1, the photoelectric signals $I_1(\theta_0)$ and $I_2(\theta_0)$ corresponding to the quantities of scattered light from the foreign particle become a ratio of substantially the same degree as the ratio of the transmittances of the pellicle 1 for the wavelengths $\lambda_1$ and $\lambda_2$ and therefore, the absolute value of $\log[I_1(\theta_0)/I_2(\theta_0)]$ does not become zero. So, if the absolute value of $\log[I_1(\theta_0)/I_2(\theta_0)]$ is greater than the aforementioned threshold value $\alpha$, it is judged that the foreign particle adheres to the lower surface (the surface opposite to the irradiated surface) of the pellicle 1 (step 58), and in the o&her cases, that is, if the absolute value of $\log[I_1(\theta_0)/I_2(\theta_0)]$ is equal to or smaller (including zero) than the threshold value $\alpha$, it is judged that the foreign particle adheres to the upper surface (the irradiated surface side) of the pellicle 1 (step 59), and the judgment as to whether the surface to which the foreign particle adheres is the upper surface or the lower surface of the pellicle 1 is output as a binarized digital signal 42 from the discrimination unit 40.

A second method of discriminating the surface to which the foreign particle adheres according to the present invention will now be described with reference to the flow chart of FIG. 6.

Light 9 of wavelengths $\lambda_1$ and $\lambda_2$ is first applied to the surface of the pellicle 1 (step 60), and the variable angle mirror 13 is driven by the central unit 34 to vary the incident angle $\theta$ of the laser beam 9 onto the pellicle 1 within a predetermined range from $\theta_A$ to $\theta$. At the same time, the regularly reflected light from the pellicle 1 for the light of wavelengths $\lambda_1$ and $\lambda_2$ is received by the photoelectric detectors 18 and 20, respectively, and the reflectances $R_1(\theta)$ and $R_2(\theta)$ for the light of respective wavelengths are found as functions of the incident angle $\theta$ (step 61).

Subsequently, the incident angle for which the ratio of the transmittances of the pellicle 1, i.e., 1 - $R_1(\theta)$ and 1 - $R_2(\theta)$, becomes greatest is determined for two cases, i.e., a case where 1 - $R_1(\theta)$ is greater than 1 - $R_2(\theta)$ and a case where 1 - $R_1(\theta)$ is smaller than 1 - $R_2(\theta)$ First, the incident angle $\theta_3$ in a case where the transmittance 1 - $R_1(\theta)$ of the pellicle 1 for the wavelength $\lambda_1$ is greater than the transmittance 1 - $R_2(\theta)$ of the pellicle 1 for the wavelength $\lambda_2$, that is, for which log $[(1 - R_1(\theta))/1 - R_2(\theta))]$ is a positive value and the absolute value of log $[(1 - R_1(\theta))/(1 - R_2(\theta))]$ becomes greatest, is determined (step 62). Likewise, the incident angle $\theta_1$ for which 1 - $R_1(\theta)$ is smaller than 1 - $R_2(\theta)$, that is, log $[(1 - R_1(\theta))/(1 - R_2(\theta))]$ is a negative value and the absolute value of log $[(1 - R_1))/(1 - R_2(\theta))]$ becomes greatest, is determined (step 63). In FIG. 1, when the incident angle is $\theta_3$, the light of wavelength $\lambda_1$ is most transmitted through the pellicle 1 within the predetermined angle range of $\theta_A$ to $\theta_B$ as compared with the light of wavelength $\lambda_2$, and in FIG. 1, when the incident angle is $\theta_1$, the light of wavelength $\lambda_2$ is most transmitted through the pellicle 1 as compared with the light of wavelength $\lambda_1$. It will be noted that if the first method of discriminating the surface to which the foreign particle adheres which is shown in FIG. 5 is carried out at the respective incident angles $\theta_3$ and $\theta_1$, discrimination of the surface to which the foreign particle adheres will become possible with higher probability.

Subsequently, in proportion as the first method of discriminating the surface to which the foreign particle adheres, the threshold value $\beta_3$ (a positive value) for the discrimination of the surface to which the foreign particle adheres is first determined from the reflectances $R_1(\theta_3)$ and $R_2(\theta_3)$ for the light of wavelengths $\lambda_1$ and $\lambda_2$ at the incident angle $\theta_3$ (step 64), and the threshold value $\beta_1$ (a positive value) is determined from the reflectances $R_1(\theta_1)$ and $R_2(\lambda_1)$ for the light of wavelengths $\lambda_1$ and $\lambda_2$ at the incident angle $\theta_1$ (step 65), and $\beta_3$ and $\beta_1$ are determined, for example, as $\beta_3 = |\log[(1 - R_1(\theta_3) + 1 - R_2(\theta_3))/2]|$ and $\beta_1 = |\log[(1 - R_1(\theta_1) + 1 - R_2(\theta_1))/2]|$, respectively.

The foreign particle to be inspected is then moved to the irradiated position Q of the laser beam 9 on the pellicle 1 (step 66). Further, the variable angle mirror 13 is driven to set the incident angle of the laser beam 9 to $\theta_3$ (step 67), whereafter the scattered light from the foreign particle for the wavelengths $\lambda_1$ and $\lambda_2$ are received by the photoelectric detectors 22 and 24 to thereby obtain photoelectric signals $I_1(\theta_3)$ and $I_2(\theta_3)$ (step 68). Likewise, the incident angle is now set to $\theta_1$ (step 69), and the photoelectric signals $I_1(\theta_1)$ and $I_2(\theta_1)$ of the scattered light from the foreign particle for the wavelengths $\lambda_1$ and $\lambda_2$ are obtained (step 70).

The surface to which the foreign particle adheres is discriminated on the basis of the thus obtained photoelectric signals $I_1(\theta_3)$, $I_2(\theta_3)$, $I_1(\theta_1)$ and $I_2(\theta_1)$ (step 71). For the foreign particle adhering to the lower surface (the surface opposite to the irradiated surface side) of the pellicle 1, the transmittance of the pellicle 1 for the light of wavelength $\lambda_1$ is greater with respect to the incident angle $\theta_3$, as shown in FIG. 1, and therefore the photoelectric signal $I_1(\theta_3)$ of the scattered light from the foreign particle for the light of wavelength $\lambda_1$ is more than that photoelectric signal $I_2(\theta_3)$ of the scattered light from the foreign particle for the light of wavelength $\lambda_2$. Also, with respect to the incident angle $\theta_1$, conversely, the transmittance of the pellicle for the light of wavelength $\lambda_2$ is greater. Accordingly, the photoelectric signal $I_2(\theta_1)$ of the scattered light from the foreign particle for the light of wavelength $\lambda_2$ is more than the photoelectric signal $I_1(\theta_1)$ of the scattered light from the foreign particle for the light of wavelength $\lambda_1$.

From this, if the ratio log $[I_1(\theta_3)/I_2(\theta_3)]$ of the photoelectric signals of the scattered light for the lights of wavelengths $\lambda_1$ and $\lambda_2$ at the incident angle $\theta_3$ is greater than the threshold value $\beta_3$ ($>0$) determined at step 64 and the ratio log $[I_1(\theta_1)/I_2(\theta_1)]$ of the photoelectric signals of the scattered light for the light of wavelength $\lambda_1$ and $\lambda_2$ at the incident angle $\theta_1$ is smaller than the negative number $-\beta_1$ of the threshold value $\beta_1$ ($>0$) determined at step 65, it is judged that the foreign particle adheres to the lower surface of the pellicle 1 (step 72). If this judgment condition (step 71) is not satisfied, the foreign particle is judged as adhering to the upper surface (the irradiated surface side) of the pellicle 1 (step 73).

Figure 5:
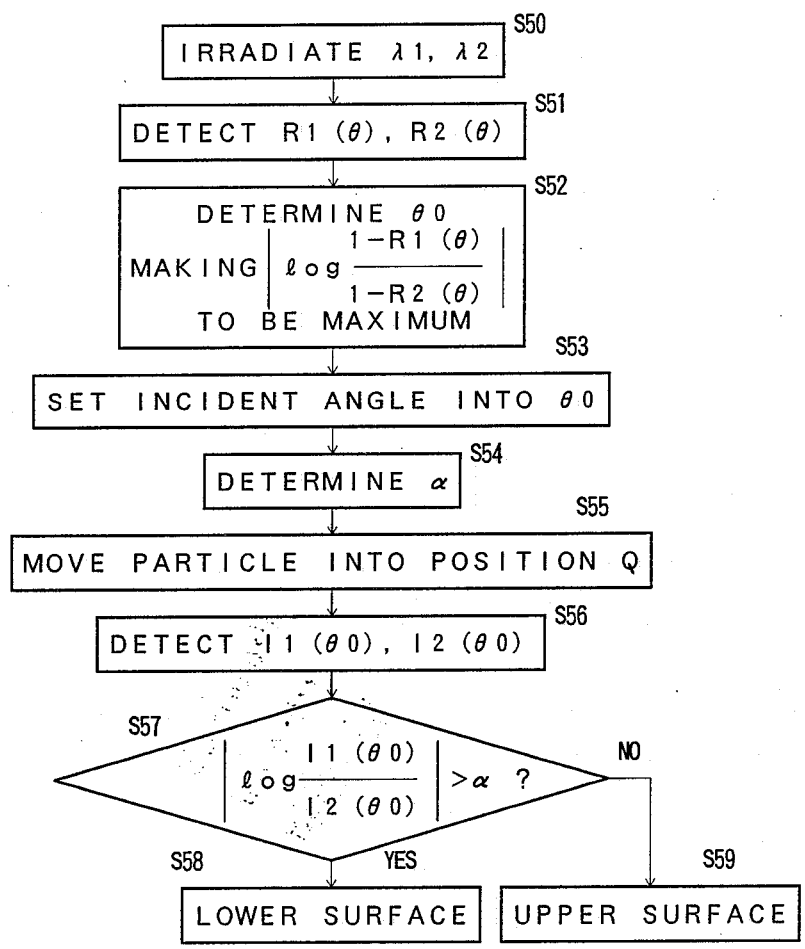
FIG. 5 is a flow chart showing a first discrimination method of discriminating the surface to which a foreign particle adheres by the use of the apparatuses of the embodiments of FIGS. 2 and 3.

In the above-described second method of discriminating the surface to which the foreign particle adheres, the surface to which the foreign particle adheres is discriminated by whether the judgment condition (step 71) is satisfied at the same time for the two incident angles $\theta_3$ and $\theta_1$ for which the ratio of the transmittances of the pellicle for the wavelengths $\lambda_1$ and $\lambda_2$ is reversed and therefore, the second method has the advantage that it is higher in discrimination probability than the first method shown in FIG. 5.

Figure 6:
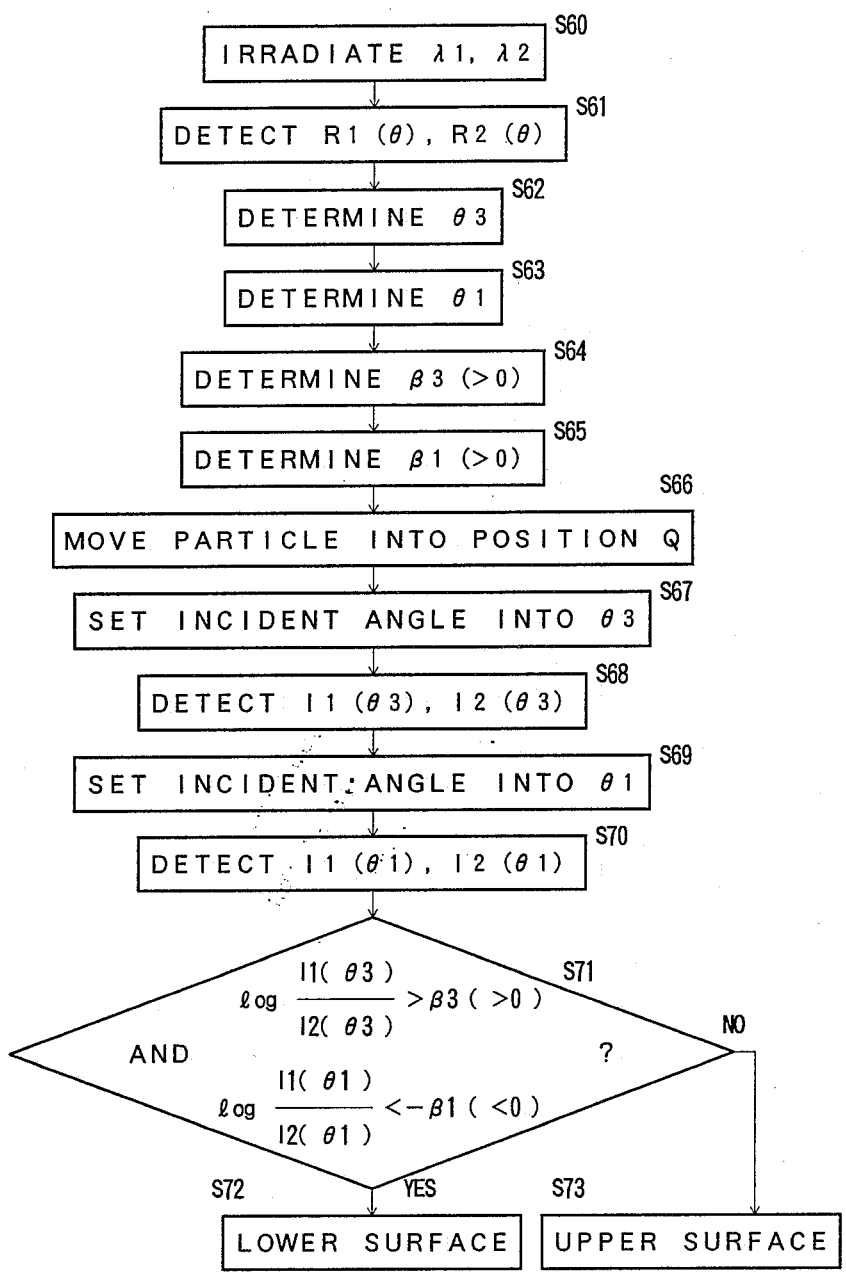
FIG. 6 is a flow chart showing a second discrimination method of discriminating the surface to which a foreign particle adheres by the use of the apparatuses of the embodiments of FIGS. 2 and 3.

When the dependency $[R_1(\theta)$ and $R_2(\theta)]$ of the light transmittances for the wavelengths $\lambda_1$ and $\lambda_2$ on the incident angle is known in advance as the film characteristic of the pellicle, the steps 50 to 54 in FIG. 5 and the steps 60 to 65 in FIG. 6 can immediately shift to steps 55 and 66, respectively, for receiving the scattered light from the foreign particle. Also, when a pellicle of the same kind is to be inspected, it is of course also possible to store in advance the incident angle and the threshold value determined during the inspection of the previous pellicle in a memory device, not shown in FIG. 4, and use the data when inspecting the pellicle of the same kind.

The construction of an apparatus according to a third embodiment of the present invention will now be described with reference to FIG. 7.

Figure 7:
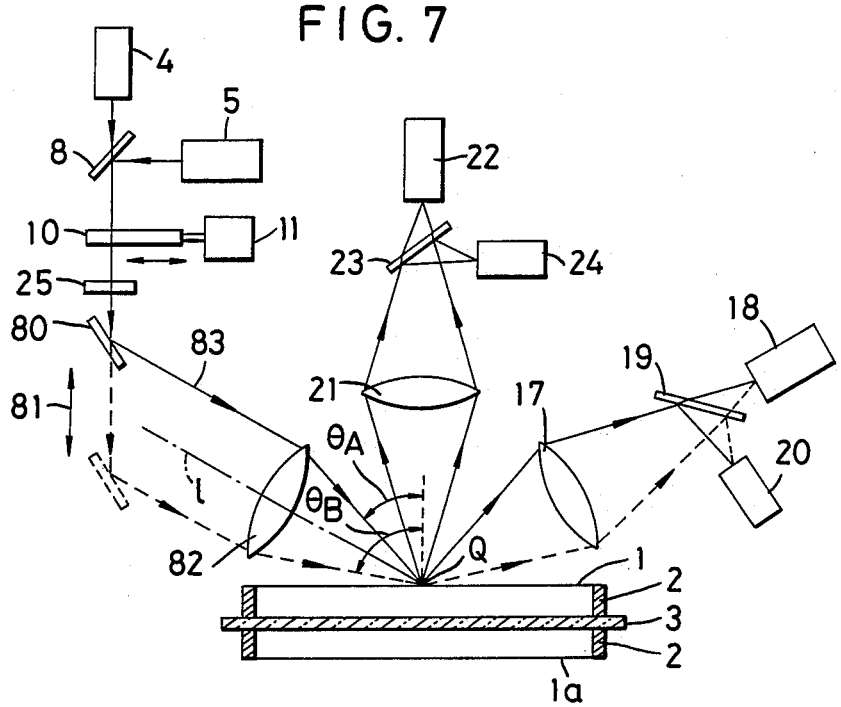
FIG. 7 schematically shows the construction of a defect inspecting apparatus according to a third embodiment of the present invention.

In FIG. 7, the constituent portions other than means for changing the incident angle of the laser beam such as the variable angle mirror 13 and the lens 16, i.e., the light source unit comprised of the laser sources 4 and 5 oscillating beams of wavelengths $\lambda_1$ and $\lambda_2$, the variable ND filter 10, the polarizing plate 25, etc., the optical system for detecting the regularly reflected light by the pellicle such as the lens 17 and the photoelectric detectors 18 and 20, and the optical system for detecting the scattered light from the foreign particle such as the light receiving lens 21 and the photoelectric detectors 22 and 24 are all the same as those in the first embodiment of FIG. 2. A lens 82 is disposed so that the irradiated position Q on the pellicle <1 is the focus position. A moving mirror 80 is movable in the direction of arrow 81 by driving means, not shown, and is set at such an angle that a reflected laser beam 83 of two wavelengths moves always in parallelism to the optic axis of the lens 82. Accordingly, the laser beam 83 after movement by the moving mirror 80 can continuously change its incident angle onto the pellicle 1 within the range of the incident angle $\theta_A$ to $\theta_B$ about the irradiated position Q by the moving mirror 80 being parallel-moved in the direction of arrow 81. This incident angle can be known from the amount of movement of the moving mirror 80 in the direction of arrow 81, and that amount of movement is measured by a measuring machine (not shown) such as a linear encoder connected to the moving mirror 80. The lens 82 for varying the incident angle may be a lens of weaker refractive powder than the lens 16 of FIG. 2, and this leads to the advantage that the construction of the lens 82 becomes simple and easy to design.

The construction of a fourth embodiment of the present invention will now be described with reference to FIG. 8.

A switch mirror 90 is disposed in the optical path between the laser sources 4, 5 outputting laser beams of wavelengths $\lambda_1$ and $\lambda_2$ and the variable ND filter 10. This switch mirror 90 is movable in the direction of arrow 91 and when it is disposed at a solid-line position as shown in FIG. 8, the laser beam 92 output from one laser source 5 is reflected and downwardly deflected by the switch mirror 90 and directed to an optical path 93. At this time, the laser beam 94 output from the other laser source 4 is intercepted by the switch mirror 90. In contrast, when the switch mirror 90 is moved to a broken-line position in FIG. 8, only the laser beam 94 is now directed to the optical path 93. That is, by putting in and out the switch mirror 90 in the direction of arrow 91, it becomes possible to select the laser beam 94 of wavelength $\lambda_1$ or the laser beam 92 of wavelength $\lambda_2$ and direct only one of these laser beams to the optical path 93.

The laser beam of single wavelength thus obtained can be caused to be obliquely incident on the pellicle 1 by the variable angle mirror 13 and the lens 16 as in FIG. 2 and can have its incident angle changed about the irradiated position Q on the pellicle 1.

In the present embodiment, the laser light incident on the pellicle 1 is the light of wavelength $\lambda_1$ or the light of wavelength $\lambda_2$ by the switch mirror 90 being put in and out in the direction of arrow 91 and therefore, the number of the photoelectric detectors for receiving the regularly reflected light 95 and the scattered light 96 from the foreign particle need not be two each for the wavelengths $\lambda_1$ and $\lambda_2$. The regularly reflected light 95 by the pellicle 1 is received by a lens 17 and a photoelectric detector 97 disposed at a position S conjugate with the irradiated position Q on the pellicle 1, and this photoelectric detector outputs a photoelectric signal proportional to the quantity of the regularly reflected light 95. On the other hand, the scattered light 96 from the foreign particle on the pellicle 1 is condensed by a light receiving lens 20 and received by a photoelectric detector 98, which outputs a photoelectric signal proportional to the quantity of the scattered light 96.

Of course, in the present embodiment, the moving mirror 80 used in FIG. 7 may be utilized instead of the variable angle mirror 13 for changing the incident angle of the laser beam onto the pellicle 1.

A processing device for the photoelectric signals output from the photoelectric detectors 97 and 98 in FIG. 8 will now be described with reference to FIG. 9.

The photoelectric outputs of the photoelectric detectors 97 and 98 are amplified by amplifiers 99 and 100, respectively, which thus output electrical signals proportional to the quantities of received light. The photoelectric detectors 97 and 98 receive the light of two wavelengths $\lambda_1$ and $\lambda_2$, but depending on the wavelength characteristics of the photoelectric detectors 97 and 98, the sensitivity to the light of wavelength $\lambda_1$ and the sensitivity to the light of wavelength $\lambda_2$ may differ from each other in some cases and therefore, the amplifiers 99 and 100 are made into VCA (voltage control amplifier) construction, and the amplification degrees of the amplifiers 99 and 100 are switched between the case of the light of wavelength $\lambda_1$ and the case of the light of wavelength $\lambda_2$ by the outputs 102 and 103 of a control unit 101 to thereby correct the difference in sensitivity to the wavelengths $\lambda_1$ and $\lambda_2$ between the photoelectric detectors 97 and 98.

The control unit 101 also effects the control of the switch mirror 90, and outputs a signal 104 so as to insert the switch mirror 90 into the optical path 93 when it is desired that the light of wavelength $\lambda_2$ be incident on the pellicle 1, and to move the switch mirror 90 in the direction of arrow 91 and dispose it at the broken-line position when it is desired that the light of wavelength $\lambda_1$ be incident on the pellicle 1. At the same time, the control unit 101 outputs signals 105 and 106 to operation units 107 and 108, respectively, and determines whether the photoelectric signals input from the amplifiers 99 and 100 are the photoelectric signal of one or the other of the light of wavelengths $\lambda_1$ and $\lambda_2$, and if it is the regularly reflected light from the pellicle for the light of wavelength $\lambda_1$, $R_1(\theta)$ obtained in the operation unit 107, and if it is the regularly reflected light from the pellicle for the light of wavelength $\lambda_2$, $R_2(\theta)$ obtained in the operation unit 107. In the same manner, in the operation unit 108, on the basis of the signal 106, $I_1(\theta)$ is obtained as a function of the incident angle $\theta$ for the light of wavelength $\lambda_1$ of the scattered light from the foreign particle, and $I_2(\theta)$ is obtained as a function of the incident angle $\theta$ for the light of wavelength $\lambda_2$. The signal processing after that, i.e., the operation of the ratio of the quantities of light in the operation units 107 and 108, the drive control of the variable angle mirror 13 by the control unit 34, and the discrimination of the surface to which the foreign particle adheres to the discrimination unit 40 are all the same as the functions of the signal processing device in the first embodiment shown in FIG. 4. Again in the fourth embodiment of FIG. 8, the method of discriminating the surface to which the foreign particle adheres may be the same method as the method shown in the flow charts of FIGS. 5 and 6.

A fifth embodiment of the present invention will now be described with reference to FIG. 10.

Figure 8:
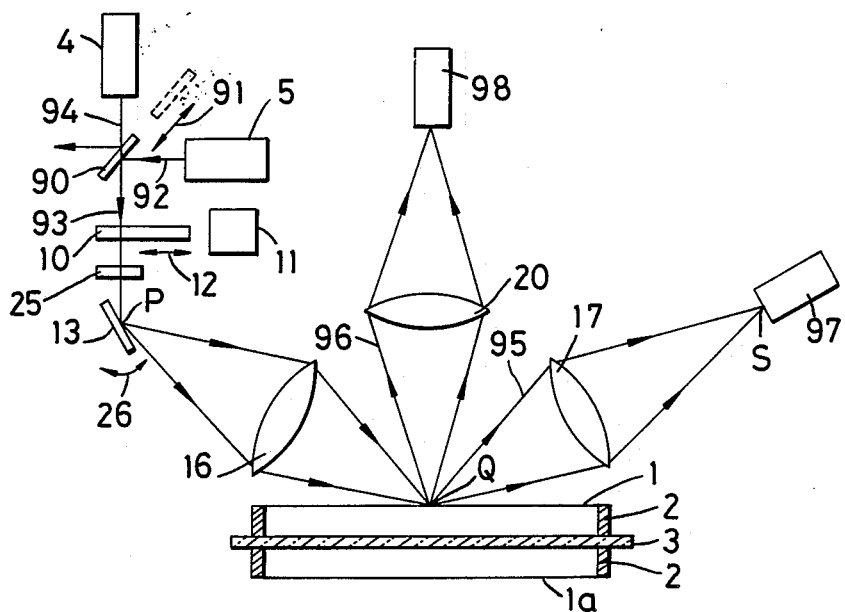
FIG. 8 schematically shows the construction of a defect inspecting apparatus according to a fourth embodiment of the present invention.
Figure 9:
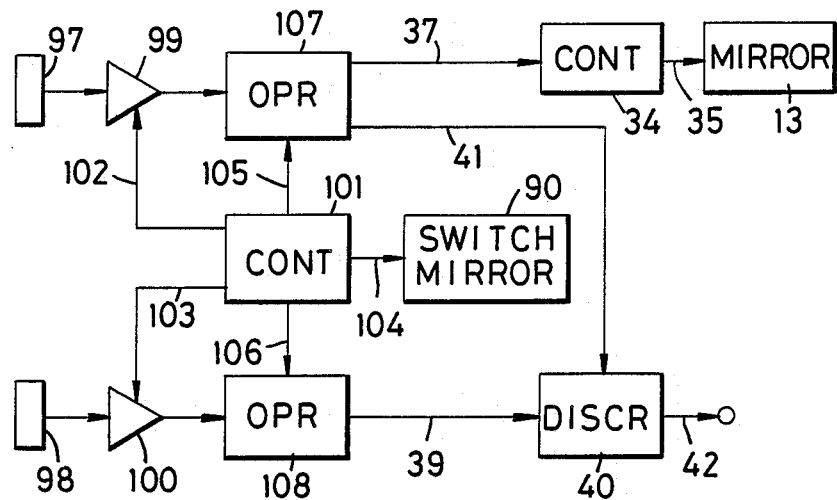
FIG. 9 is a circuit block diagram showing the construction of a signal processing circuit applied to the apparatus of the FIG. 8 embodiment.
Figure 10:
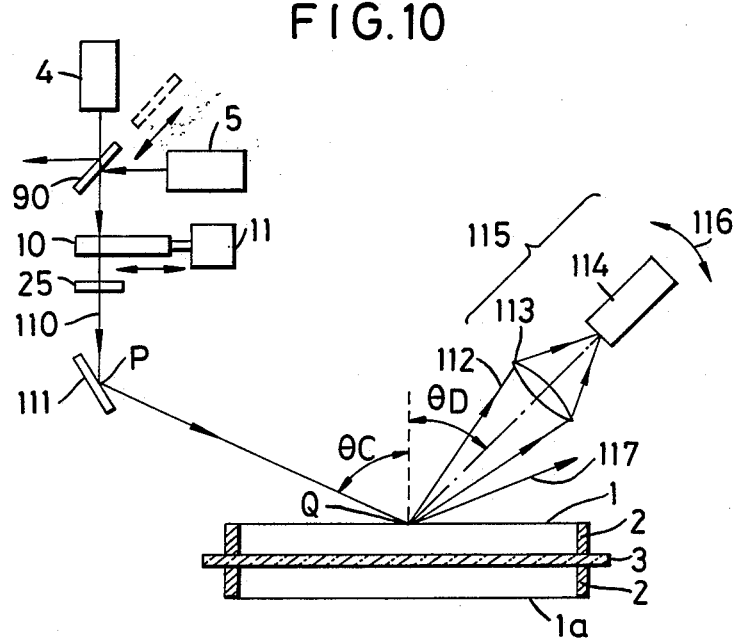
FIG. 10 schematically shows the construction of a defect inspecting apparatus according to a fifth embodiment of the present invention.

In FIG. 10, a light source unit comprised of laser sources 4 and 5, a switch mirror 90, a variable ND filter 10, a polarizing plate 25, etc. is the same as that in the fourth embodiment shown in FIG. 8. A laser beam 110 of wavelength $\lambda_1$ or wavelength $\lambda_2$ obtained from the light source 4 or 5 is deflected by a fixed mirror 111 and applied to a point Q on the pellicle 1 at a suitable incident angle $\theta_C$. Scattered light 112 obtained from a foreign particle adhering to the point Q on the pellicle I is received by a light receiving unit 115 comprised of a light receiving lens 113 and a photoelectric detector 114, which thus outputs a photoelectric signal proportional to the quantity of light received.

The light receiving unit 115 is movable in the direction of arrow 116 about the point Q relative to the pellicle 1 by driving means, not shown. The light receiving unit 115 may be disposed at any position as long as the position is a position at which the regularly reflected laser beam 117 of the incident laser beam 110 be the pellicle 1 is not incident on the light receiving lens 113 and scattered light passes. Also, the variable range of the light receiving angle $\theta_D$ of the light receiving unit 115 may be moved in any manner if it is a range in which the regularly reflected laser beam is not incident on the light receiving lens 113. Actually, however, the light receiving angle $\theta_D$ is better in the accuracy of discrimination of the surface to which the foreign particle adheres (discrimination probability) if it is in a wide range, and may preferably be the range of 0°–90°.

The method of discriminating the surface to which the foreign particle adheres based on this fifth embodiment will hereinafter be described. If a foreign particle adheres to the upper surface or the lower surface of the pellicle, the quantity of the scattered light 112 created from the foreign particle varies as the light receiving unit 115 is driven to change the light receiving angle $\theta_D$. Generally, the scattering characteristic is such that the quantity of forward scattered light is greater than the quantity of rearward scattered light and therefore, the greater is the light receiving angle $\theta_D$, the greater is the quantity of scattered light received. If a foreign particle adheres to the upper surface of the pellicle 1, when a laser beam of either of wavelengths $\lambda_1$ and $\lambda_2$ is applied to the foreign particle, the scattering characteristic thereof is the same for the wavelength $\lambda_1$ or the wavelength $\lambda_2$. In contrast, the scattered light from a foreign particle adhering to the lower surface of the pellicle 1 is received after being transmitted through the pellicle 1 and therefore, where the transmittance of the pellicle 1 differs for the wavelength $\lambda_1$ and the wavelength $\lambda_2$, a different scattering characteristic is exhibited when the light receiving angle $\theta_D$ is changed. Accordingly, the switch mirror 90 is moved and the light receiving unit 115 is driven by driving means 117, and the light receiving angle $\theta_D$ is changed and the scattered light from the foreign particle by the laser beam of wavelength $\lambda_1$ and the scattered light from the foreign particle by the laser beam of wavelength $\lambda_2$ are received, and if the variation in the quantity of the scattered light for the light receiving angle $\theta_D$ differs in the case of each wavelength, it is possible to judge that the foreign particle adheres to the lower surface of the pellicle 1, and if said variation is the same, it is possible to judge that the foreign particle adheres to the upper surface of the pellicle 1. Accordingly, in the present embodiment, even if the two sets of four photoelectric detectors shown in FIG. 2 are not provided, substantially the same effect can be obtained by the photoelectric detector which subtends the point Q on the pellicle 1 from only a single direction.

In each of the above-described embodiments of the present invention, with a foreign particle whose position of adherence on the pellicle is already clear as an object, to which of the upper surface (the irradiated surface side) or the lower surface (the surface opposite to the irradiated surface side) of the pellicle the foreign particle adheres has been discriminated, but it is possible to add the function of generally inspecting the pellicle and thereby detect the presence of a !foreign particle and the position thereof on the pellicle, and then move said foreign particle onto the laser-irradiated position Q on the pellicle by suitable moving means and effect the discrimination of the surface to which the foreign particle adheres. Or it is also possible to effect said discrimination simultaneously with the general inspection. This leads to the advantage that it becomes possible to automatic the detection of the foreign particle and the discrimination of the surface to which it adheres and further, if the apparatus of the present embodiment is incorporated into a microscope as previously described, the observation of the size or the like of the foreign particle also becomes possible.

Also, the laser sources 4 and 5 in each embodiment may be a suitable combination of a gas laser, a solid laser, a semiconductor laser, etc. which have a desired oscillation wavelength.

As previously described, a system for the detection of a foreign particle disclosed in the aforementioned U.S. Pat. No. 4,468,120 can be applied as the technique of inspecting the presence of a foreign particle adhering to the pellicle and two-dimensionally detecting the position of adherence thereof. In the system disclosed in this patent, a laser beam is caused to be obliquely incident and is one-dimensionally scanned and an object to be inspected is sub-scanned and the scattered light from the foreign particle is photoelectrically detected from multiple directions to thereby accomplish the detection of the foreign particle, and the main scanning position of beam scan and the subscanning position of the object to be inspected are found to determine the adherence coordinates position of the foreign particle. If such a foreign particle inspecting apparatus and the apparatus of each embodiment of the present invention are combined, to which of the front and back surfaces of the pellicle the foreign particle adheres an be found within a very short time and with high accuracy (high probability).

Also, the laser beams themselves from the laser sources 4 and 5 shown in each embodiment may be used to provide an oblique incident type foreign particle inspecting apparatus. In such case, it is necessary to provide a beam scanner such as a polygonal mirror or a galvano mirror to scan one-dimensionally while keeping the angle of the variable angle mirror 13 determined by the control unit 34, i.e., the predetermined incident angle of the laser beams (wavelengths $\lambda_1$ and $\lambda_2$) Also, the lenses 16 and 21 (or the lens 82) may be cylindrical lenses having their generatrices made coincident with the scanning direction of the beam. Also, in each embodiment of the present invention, an aperture such as a slit may effectively be provided at a position in the light receiving system which is conjugate with the pellicle surface (point C) to thereby prevent multiplex reflected light from the pellicle surface or the reticle surface from being photoelectrically detected as stray light.

What is claimed is:

1. A defect inspecting apparatus for determining the presence of a defect element adhering to either of the front and back surfaces of a thin film-like object to be inspected having a light-transmitting property, comprising: applying means for applying two light beams of different wavelengths to one surface of said object to be inspected along an optical path leading to said object; incident angle varying means for varying the incident angle of said two light beams onto said one surface; first photoelectric detector means for receiving light of said two light beams reflected by or transmitted by said object to be inspected; second photoelectric detector means for receiving light of said two light beams scattered by said defect element; and discriminating means for discriminating the surface of said object to be inspected to which said defect element adheres on the basis of a detection output of said first photoelectric detector means and a detection output of said second photoelectric detector means.

2. A defect inspecting apparatus according to claim 1, wherein said applying means includes a pair of laser sources emitting light beams of different wavelengths, respectively, and a variable density filter provided on a common optical path through which said two light beams pass.

3. A defect inspecting apparatus according to claim 1, wherein said applying means includes a pair of laser sources emitting light beams of different wavelengths, respectively, and a polarizing plate for polarizing said light beams to s-polarization light obliquely incident on said object to be inspected.

4. A defect inspecting apparatus according to claim 1, wherein said object to be inspected is a pellicle covering a reticle to isolate the surface of the reticle from the outside and disposed with a space provided from the surface of the reticle by a support frame, and said applying means applies said light beams from the side of said pellicle away from said reticle.

5. A defect inspecting apparatus according to claim 1, wherein said applying means includes a pair of laser sources emitting intersecting light beams of different wavelengths, respectively, and a dichroic mirror at the intersection of said light beams, said mirror having a wavelength selecting property and transmitting therethrough one of the light beams of said pair of laser sources and reflecting the other light beam, so that both of said light beams are directed along said path, and said incident angle varying means includes a projection lens for obliquely projecting said two light beams onto said object to be inspected, and an angle variable mirror obliquely disposed on said optical path for directing said two light beams rom said dichroic mirror to said projection lens and having a rotation center at a position conjugate with said object to be inspected with respect to said projection lens.

6. A defect inspecting apparatus according to claim 1, wherein said applying means includes a pair of laser sources emitting intersecting light beams of different wavelengths, respectively, and a dichroic mirror at the intersection of said light beams, said mirror having a wavelength selecting property and transmitting therethrough one of the light beams of said pair of laser sources and reflecting the other light beam, so that both of said light beams are directed along said path, said incident angle varying means includes a projection lens for obliquely projecting said two light beams onto said object to be inspected and a movable mirror obliquely disposed on said optical path for guiding said two light beams from said dichroic mirror to said projection lens, said movable mirror being movable along a portion of said optical path extending from said dichroic mirror in order to vary the position of a portion of said optical path extending from said movable mirror to said projection lens while maintaining the same direction of the last-mentioned portion.

7. A defect inspecting apparatus according to claim 1, wherein said applying means includes a pair of laser sources emitting intersecting light beams of different wavelengths, respectively, and a dichroic mirror at the intersection of said light beams, said mirror having a wavelength selecting property and transmitting therethrough one of the light beams of said pair of laser sources and reflecting the other light beam, so that both of said light beams are directed along said path, said first photoelectric detector means includes a first condensing lens for condensing regularly reflected light or transmitted light of said two light beams, a dichroic mirror for resolving said regularly reflected light or said transmitted light condensed by said first condensing lens into a pair of resolved light beams of different wavelengths, and a pair of photoelectric detectors for receiving said resolved light beams, and said second photoelectric detector means includes a second condensing lens for condensing scattered light of said two light beams, a dichroic mirror for resolving said scattered light condensed by said second condensing lens into a pair of resolved light beams of different wavelengths, and a pair of photoelectric electric detectors for receiving the last-mentioned resolved light beams.

8. A defect inspecting apparatus according to claim 1, wherein said applying means includes a pair of laser sources emitting light beams of different wavelengths, respectively, and a movable mirror movable into and out of said optical path to cause said two light beams of different wavelengths from said pair of laser sources to be applied to said surface of said object alternately, said photoelectric detector means includes a first condensing lens for condensing regularly reflected light or transmitted light of either of said two light beams, and a first photoelectric detector for receiving regularly reflected light or transmitted light condensed by said first condensing lens, and said second photoelectric detector means includes a second condensing lens for condensing scattered light of either of said two light beams, and a second photoelectric detector for receiving said scattered light condensed by said second condensing lens.

9. A defect inspecting apparatus for determining the presence of a defect element adhering to either of the front and back surfaces of a thin film-like object to be inspected having a light-transmitting property, comprising: a pair of laser sources emitting light beams of different wavelengths, respectively, light beam switching means for alternately selecting said two light beams of different wavelengths, applying means for obliquely applying each light beam selected by said light beam switching means to a position on one surface of said object to be inspected at a predetermined angle; photoelectric detector means for receiving light of each selected light beam scattered by said defect element, driving means for displacing said photoelectric detector means angularly about said position on said object to be inspected; and discriminating means for discriminating the surface of said object to be inspected to which said deflect element adheres on the basis of two detection outputs of said photoelectric detector means produced in response to the alternate reception of scattered light of said two light beams of different wavelengths.

10. A defect inspecting apparatus according to claim 9, wherein said photoelectric detector means includes a condensing lens for condensing the scattered light from said defect element, and a photoelectric detector having a light receiving surface at a position conjugate with said position on said object to be inspected with respect to sad condensing lens and receiving said scattered light condensed by said condensing lens.

11. A defect inspecting apparatus according to claim 9, wherein said applying means includes a variable density filter provided on said optical path and through which said two light beams pass, a polarizing plate for polarizing said light beams to S-polarization light incident on said object to be inspected, and a fixed mirror obliquely disposed on said optical path for reflecting said two light beams so that said two light beams are obliquely incident on said object to be inspected.

12. An apparatus for inspecting a foreign particle on a light-transmitting pellicle, comprising:
- means for applying two light beams of different wavelengths to one surface of said pellicle;
- means for determining the incident angle of said two light beams onto said one surface of said pellicle and thereby determining the difference between the transmittances of said two light beams in said pellicle;
- means for receiving light of said two light beams reflected by or transmitted by said pellicle and producing a corresponding first output;
- means for receiving light of said two light beams scattered by said foreign particle and producing a corresponding second output; and
- means for discriminating the surface of said pellicle on which said foreign particle exists on the basis of said first and second outputs.

13. An apparatus according to claim 12, wherein said determining means determines said incident angle for which the difference between the transmittances of said two light beams in said pellicle is greatest.

* * * * *